United States Patent [19]

Kresse et al.

[11] Patent Number: 5,427,767
[45] Date of Patent: Jun. 27, 1995

[54] NANOCRYSTALLINE MAGNETIC IRON OXIDE PARTICLES-METHOD FOR PREPARATION AND USE IN MEDICAL DIAGNOSTICS AND THERAPY

[75] Inventors: Mayk Kresse; Rudiger Lawaczeck; Detlef Pfefferer, all of Berlin, Germany

[73] Assignee: Institut für Diagnostikforschung GmbH an der Freien Universität Berlin, Berlin, Germany

[21] Appl. No.: 882,130

[22] Filed: May 13, 1992

[30] Foreign Application Priority Data

May 28, 1991 [DE] Germany .................. 41 17 782.7

[51] Int. Cl.⁶ ............................................. A61B 5/055
[52] U.S. Cl. ...................... 424/9.32; 436/173; 514/54; 514/56; 128/653.4; 424/9.322
[58] Field of Search ............... 424/9; 436/173, 806; 514/54, 56; 128/653.4

[56] References Cited

U.S. PATENT DOCUMENTS

| | | | |
|---|---|---|---|
| 4,101,435 | 7/1978 | Hasegawa et al. | 252/62.53 |
| 4,247,406 | 1/1981 | Widder et al. | 252/62.53 |
| 4,267,234 | 5/1981 | Rembaum | 428/403 |
| 4,452,773 | 6/1984 | Molday | 424/1.1 |
| 4,731,239 | 3/1988 | Gordon | 424/9 |
| 4,735,796 | 4/1988 | Gordon | 424/9 |
| 4,758,429 | 7/1988 | Gordon | 424/85 |
| 4,767,611 | 8/1988 | Gordon | 424/9 |
| 4,770,183 | 9/1988 | Groman | 128/654 |
| 5,055,288 | 10/1991 | Lewis et al. | 424/9 |
| 5,141,739 | 8/1992 | Jung et al. | 424/4 |
| 5,143,716 | 9/1992 | Unger | 424/9 |
| 5,155,215 | 10/1992 | Ranney | 534/16 |
| 5,160,725 | 11/1992 | Pilgrimm | 424/9 |
| 5,169,631 | 12/1992 | Rase | 424/401 |
| 5,213,788 | 5/1993 | Ranney | 424/9 |

FOREIGN PATENT DOCUMENTS

| | | |
|---|---|---|
| 0186616 | 7/1986 | European Pat. Off. . |
| 0361960 | 4/1990 | European Pat. Off. . |
| 0423002A1 | 10/1990 | European Pat. Off. . |
| 0444194A1 | 9/1991 | European Pat. Off. . |
| WO83/01738 | 5/1983 | WIPO . |
| WO89/11154 | 11/1989 | WIPO . |
| WO90/01295 | 2/1990 | WIPO . |
| WO91/15753 | 10/1991 | WIPO . |
| WO91/61080 | 10/1991 | WIPO . |

Primary Examiner—Gary E. Hollinden
Attorney, Agent, or Firm—Nixon & Vanderhye

[57] ABSTRACT

The invention relates to nanocrystalline magnetic particles consisting of magnetic iron oxide core of $Fe_3O_4$, gamma-$Fe_2O_3$ or mixtures thereof and an envelope chemisorbed to said core, the method for preparation of these particles as well as the use thereof in medical diagnostics and/or therapy. The magnetic particles, according to the invention, are characterized by composition of the coating material of natural or synthetic glycosaminoglycans and/or their derivatives with molecular weights of 500 Da to 250,000 Da, if necessary, covalently cross-linked with appropriate cross-linking agents and/or modified by specific additives.

11 Claims, 4 Drawing Sheets

Fig. 2 TIME DEPENDENCE 20 μmol Fe/kg
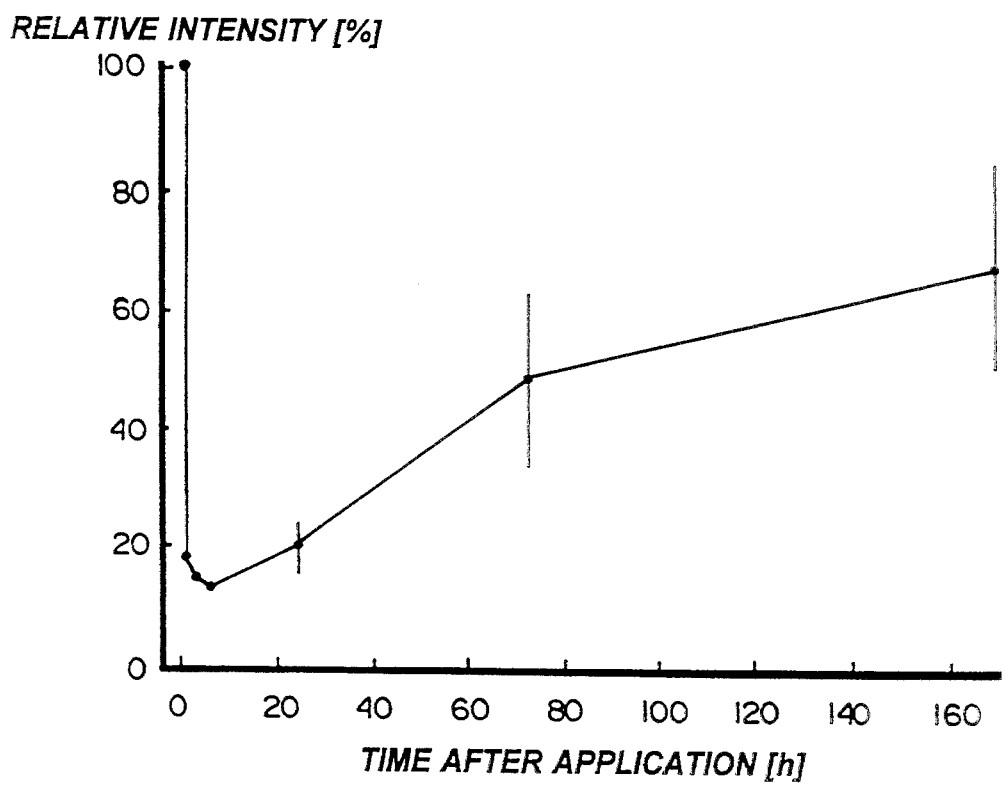
Fig. 3 DOSAGE DEPENDENCE AFTER APPLICATION
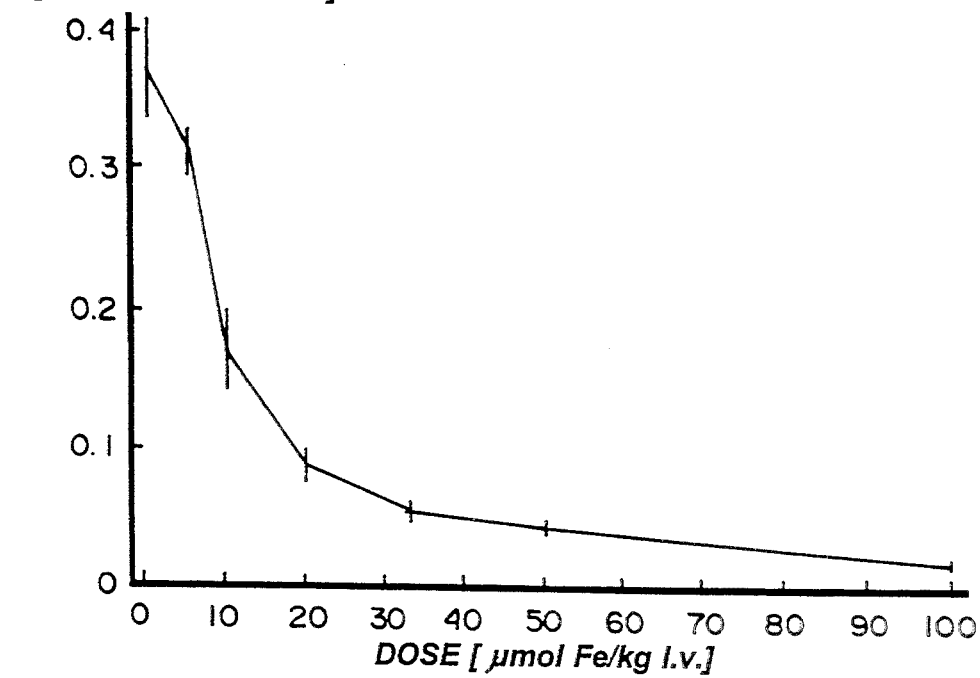

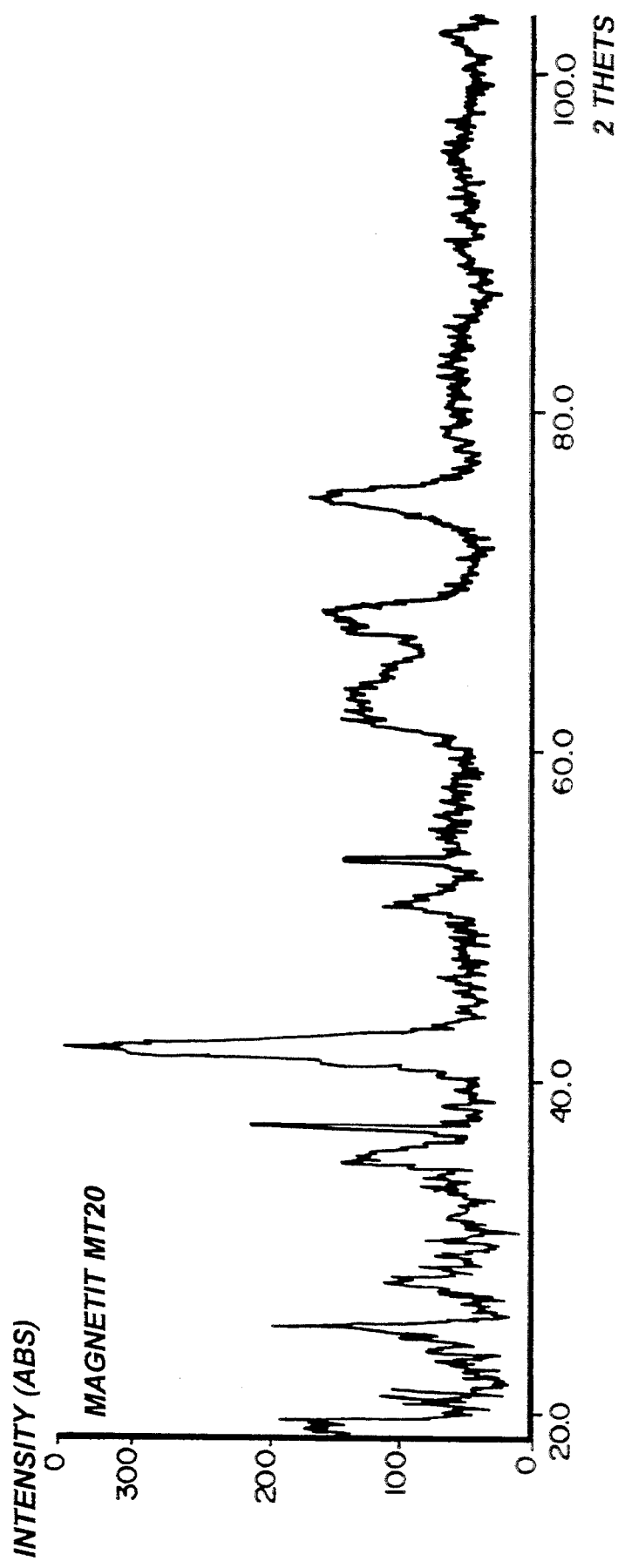

NANOCRYSTALLINE MAGNETIC IRON OXIDE PARTICLES-METHOD FOR PREPARATION AND USE IN MEDICAL DIAGNOSTICS AND THERAPY

The invention relates to nanocrystalline magnetic particles consisting of a magnetic iron oxide core of $Fe_3O_4$, gamma-$Fe_2O_3$ or a mixture thereof and a chemisorbed coating as well as its aqueous colloid dispersion solution, the method for the preparation of these particles as well as the use thereof in medical diagnostics and therapy.

Magnetic substances have found their way into medical use as contrast media for magnetic resonance imaging. It should be noted that the first substance to be approved for use was a Gd-DTPA complex (Magnevist ®). Magnetic iron oxide particles have proven to be especially effective in liver diagnostics. They are now in the pre-clinical and also, to some extent, in the clinical development stage. The substances in question are primarily ferrimagnetic iron oxides (e.g. magnetite), nanoparticles which are surrounded with a coating to form stable aqueous sols.

Besides their use as diagnostic agents, ferrous/ferrimagnetic particles are playing an increasing role in the in vitro separation technique and as "thermoseeds" in local hyperthermia.

Numerous magnetite preparation processes and uses are described in the scientific and patent law literature.

Hasegawa and Hokkoku (U.S. Pat. No. 4,101,435) describe an iron oxide-dextran complex and its preparation.

Rembaum (U.S. Pat. No. 4,267,234) refers to magnetic polyglutaraldehyde microparticles which are prepared by suspension polymerization in the presence of magnetic particles. Widder and Senyei (U.S. Pat. No. 4,247,406) prepare microparticles from an amino acid-polymer matrix in which magnetic particles are embedded. A similar method with nanoparticles is used by Schröder and Mosbach (WO 83/01738) whereby a crystalline hydrocarbon matrix surrounds the magnetic material. Groman and Josephson (U.S. Pat. No. 4,770,183) use magnetic metal oxide particles which are non-coated and coated with a polysaccharide and/or protein coating. Molday (U.S. Pat. No. 4,452,773) describes the synthesis of ferromagnetic iron oxide cores with a polysaccharide coating. He achieves a stable sol and can couple proteins to the dextran coating using periodate activation.

Gordon (U.S. Pat. No. 4,731,239) claims the use of ferrous, para- and diamagnetic particles of iron hydroxide, iron oxide and iron dextran for diagnostic purposes. Additional patents (U.S. Pat. Nos. 4,767,611; 4,758,429; 4,735,796) focus on diagnosis and therapy with the aid of the aforesaid iron dextran or iron transferric dextran particles and alternating electromagnetic fields. The particles can be directed to their targets by antigens, antibodies, enzymes or prosthetic groups. Gries et al. (EP 186616) use magnetic particles of double metal oxide/hydroxide and a complex agent of proteins or alkaline treated saccharides or polysaccharides.

Over the years the complexity of the particles has increased and the target has become more specific. Ranney (EP-361960) uses polyatomic chrome complexes which are bonded to a biocompatible clearable carrier.

The carriers listed are: hydrocarbons, polysaccharides, glycosaminoglycans and structurally analogous synthetic polymers.

These $Cr_4$ S clusters have the disadvantage that the number of unpaired electrons is limited to 12.

Application in diagnostics is complemented by therapeutic aspects (hyperthermia, chemotherapy).

Menz et al. (WO 9001295) aim at a special cellular uptake mechanism (receptor-mediated endocytosis) with their superparamagnetic contrast media. They use magnetic iron oxide particles which are surrounded by an arabinose galactan coating of vegetable extraction the toxicological safety of which has not as yet been confirmed.

Yudelson (WO 8911154) deposits a coating of gelatin and a polymeric acid (preferably gum arabic) on the superparamagnetic particles using coacervation and cross-linking preferably with glutaraldehyde. Pilgrim (European patent application publication number 0284549) uses a different approach by forming a chemical bond between the magnetite surface and synthetic polymer stabilizer substances. The reactive stabilizer substance is chemically bonded to the superparamagnetic particles using phosphate, phosphonate or carboxylate groups. Tissue specific bonding substances can be added to the polyethylene skeleton of the stabilizer substance.

In both cases, preparation and magnetic properties of the superparamagnetic particles are described without furnishing proof of the medical suitability and tolerance of the particles.

Magnetic materials are classified as dia-, para-, or ferromagnetic according to their properties in a magnetic field. Dia- and paramagnetism are atomic/molecular properties which are based on the magnetic moment of the electron. The diamagnetism is based on orbital motion of the electrons and is induced by the applied magnetic field. The magnetization is aligned inversely to the external magnetic field. Paramagnetic substances are characterized by one or more unpaired electrons, magnetization is aligned parallel to the external field. Hence paramagnetic atoms/molecules have a permanent magnetic moment and without an external field these magnetic moments are not oriented. The susceptibility is independent of the applied field and is inversely proportional to temperature (Curie's law).

In solid bodies, strong interaction may develop between adjacent atoms/ions so that spontaneous magnetization results. One generally refers to ferromagnetism with more accurate classification in ferrous, ferric and antiferromagnetism. Examples of ferromagnetic materials are the metals iron, cobalt, nickel, many rare earth elements as well as their alloys. The magnetic moment of adjacent atoms/ions can be aligned anti-parallel in combinations of different types of atoms, of ions with different oxidation numbers or of ions that are constructed on a different lattice position. Complete suspension of spontaneous magnetization is referred to as antiferromagnetism. Partial suspension is referred to as ferrimagnetism. Ferrite with a spinel structure demonstrates ferrimagnetic properties. In all three cases domains are formed in solid bodies with different alignments of spontaneous magnetization. Without an external field the magnetic moments of the domains are randomly distributed and there is no externally directed total magnetic moment. Magnetic moments of the domain are aligned in the external magnetic field. A condition preserved in the permanent magnet even after disconnection of the external magnetic field. This is referred to as remanence. The thermal energy counteracts a spontaneous parallel/antiparallel alignment of the individual magnetic moments in particles which are smaller than the domain. Suspensions of such ferrous-/ferrimagnetic particles with dimensions smaller than 10–50 nm have properties similar to paramagnetic materials. They show no remanence or hysteresis but they show susceptibility values which approach the corresponding values for the solid body. Therefore, they are often referred to as superparamagnetic particles. Ferrites which have been used as parenteral MR contrast media are included in this category (e.g. Wolf et al., Magnetic Resonance Annual, New York, Raven Press 1985, 231–266; Saini et al., Radiology 1987, 162,217–222).

The MR image and signals of MR spectroscopy are produced due to interaction of three physical parameters: density of the sort of core involved (e.g. protons, $^{13}$ carbon, $^{31}$ phosphorous), spin-lattice-relaxation time, $T_1$, and spin-spin-relaxation time, $T_2$. $T_1$ and $T_2$ affecting signal intensity in a complicated manner. They are functions of strength of the magnetic field, temperature, reorientation and the type of physical interaction among individual molecules. Signal intensity increases proportionally to the density of the observed core. For protons the observed cores can be roughly subdivided between fat and water protons. Proton density in a physiological environment can only be slightly influenced, e.g. by deuterium oxide substitution. Relaxation time, on the other hand, can be relatively easily influenced by additional paramagnetic molecules/ions (molecules with unpaired electrons, e.g. spin probes or ions of rare earth elements). The underlying relaxation mechanisms, e.g. by paramagnetic ions, are fairly well understood and are found in relevant monographs and text books (Solomon-Bloembergen equation).

Physical description of the relaxation effect is more difficult in the case of particular active substances, especially when these are not homogeneously distributed. Influence on $T_2$ time is predominant with ferric/ferromagnetic iron oxide particles. This may result in signal boosting up to complete signal extinction, depending on the given concentration of iron oxide particles and the chosen pulse sequence. Normally, relaxation-time-shortening properties of MR contrast media are expressed by relaxivity. Good—molecularly dissolved—paramagnetic substances have values of appx. 4 1/mmol $\phi$s (Gd-DTPA) for $T_1$ and $T_2$ relaxivity at 0.47 T in water and 40° C. The dispersions of superparamagnetic magnetite or maghemite are appx. 20–40 for the $T_1$ and appx. 200 for the $T_2$ relaxivity. Size, coating, the amount of gamma-$Fe_2O_3$ and the degree of the recuperation of crystalline fault sites contribute to the individual value.

Pure magnetic iron oxide particles which could possibly be used as diagnostic agents in nuclear magnetic resonance imaging aggregate in aqueous solution with neutral pH and do not form a stable and parenterally injectable sol. The balance of forces among the particles can be so shifted by coating the magnet core with appropriate substance that the thermal energy (Brownian motion) counteracts the aggregation and sedimentation and a stable gel can be obtained. A number of substances which can be used in this manner are known from the literature and patents.

The coating must provide for a stable suspension. Heat sterilization and/or sterile preparation should be possible in the context of a galenic formulation. In addition, the particles must be of medical diagnostic and/or therapeutic value. Moreover, they must be pharmacologically and toxicologically safe. Most of the coating substances fail to fulfill these criteria.

So far dextran encapsulated iron oxides are the furthest developed of all the ferrimagnetic nanoparticles mentioned. Clinical development has been cancelled in the US due to side effects (e.g. drop in blood pressure) (G. L. Wolf "Current status of MR imaging contrast agents: special report", Radiology 172, 709–710 (1989)). These dextran magnetites are currently being thoroughly tested by the FDA (Food and Drug Administration) (Diagnostic Imaging, October 1990). Dextran magnetites are instable against mixtures with common solvents. Galenic stability in physiological NaCl solution cannot be maintained either over extended periods of time. Derivatization is limited or only possible under drastic conditions. Physiologically, dextran has an adverse allergic potential; the same being true for protein coated magnetites.

The medical diagnostic usefulness of coated ferric-/ferromagnetic (superparamagnetic) iron oxide particles (parent substance) is based on the fact that, following intravenous injection, they are taken up by phagocytizing monocytes and macrophages of the reticuloendothelial system (RES) of the clinically intact splenic and hepatic tissue but are not taken up by tumors and metastases. With normal spin-echo sequences such locally differentiated uptake leads to signal extinction in the magnetic resonance image of the clinically intact splenic and hepatic tissue shortly after parenteral application. Whereas tumors and metastases in liver and spleen appear bright against dark background. A similar effect is also found in tumors and metastases in the lymphatic system.

Presently, efforts are being made to avoid singular uptake of liposomes and other particular drug carriers via mononuclear phagocytizing cells (RES). This is important for selective enrichment of tumors/tissues in diagnostics and therapy.

The therapeutic benefit of the aforesaid iron oxide particles is based on the applicability of iron preparations as anti-anemic drugs as well as in magnetic targeting, a possibility of targeted transport of iron oxide particles and adhering substances to the site of action by means of external magnetic fields. Recoil-free sensitization by gamma rays and intracellular H-field coupled hyperthermia are additional applications of the iron oxide particles. Resonant nuclear absorption of gamma quanta with subsequent re-emission or emission of Auger electrons is referred to as the Mössbauer effect after its discoverer. Utilization of this effect in radiotherapy was described by Mills et al. (Nature 336, 787–789, 1988).

In contrast to the iron oxide sols described herein, Mills uses molecularly dissolved substances which in solution show only a negligible recoil-free Mössbauer effect and consequently a resonance strengthened radiotherapeutic benefit. The advantages of resonant nuclear absorption of gamma-quanta with subsequent re-emission or emission of Auger electrons are obvious. The primary radioactive source is outside of the body and the non-radioactive sensor is introduced to the tumor tissue. Absorption of gamma quanta by the non-radioactive radiation sensors without significant stress on the surrounding tissue is the primary result which is attributable to the large capture cross section of the resonant core absorption. These radiation sensors (antennae) can be placed in the tumor tissue (preferably intracellularly). The radioactive source (transmitter) and the receiver are tuned to each other and must satisfy physical and radiobiological criteria. On the receiving end 57Fe, 99Ru, 119Sn, 121Sb, 127I, 151Eu, and 157Gd are preferred possible substances, all of which are not radioactive. Ferrites and magnetites can be doped with the aforesaid Mössbauer isotopes without significant impact on physical properties.

Further use of ferromagnetic materials is based on the assumption that magnetic materials can be introduced into the tumor in the form of small particles and externally heated by coupling of electromagnetic alternating fields through eddy current, hysteresis losses in the course of magnetic reorientation. Controllable energy uptake is possible through choice of the Curie point (Curie temperature) based on the composition of the magnetic particles (cf. Lilly et al., Radiology 154, 243-244 (1985)). In either case, particles with dimensions larger than each of the single domains should be used for energy uptake. Here, a compromise will have to be made between the physically necessary and pharmacologically tolerable particle dimension, depending on the mode of application. However, based on electron microscopic images of tissue sections the conclusion may be drawn that nanocrystalline particles also tend to aggregate into larger complexes following intracellular uptake so that these nanocrystalline particles may also be considered for this application. Moreover, initial measurements on phantoms indicate that there are also physical mechanisms which can lead to heating of single domain particles.

Another possible approach to therapy can be taken by insertion of 157Gd into ferrites and accomplishing neutron activation for thermal and epithermal neutrons taking advantage of the large capture cross section of 157Gd. As in resonant nuclear absorption through photons (Mössbauer) described above, tissue containing no 157Gd will scarcely take up neutrons and consequently will not be detrimentally affected. Neutron uptake is primarily concentrated on the areas containing 157Gd. Hence, sufficient enrichment of the tumor provided, radiation damage is inflicted only on the tumor by secondary radiation (Auger electrons and photons). The particles must be doped with the appropriate isotopes for application of ferrite/magnetite in therapy. The degree of doping of ferrite/magnetite as well as size, charge, hydrophobicity and possibly targeting should be adjusted to the purpose of the therapy. Macrophages are known to take up iron oxide particles and other foreign substances and to undergo concentration on the periphery of tumors. It is also possible to concentrate substances in specific tumors by attaching them to monoclonal antibodies. This enables targeting of radiation in order to inhibit the tumor growth and/or perform therapeutic hyperthermia. In addition, a positive contribution can be made to synovectomy through extracorporeal and/or intracorporeal radiation sensitization. Moreover, even slight accumulation of macrophages containing iron oxide in the vicinity of a tumor can be used for tumor detection by means of highly sensitive magnetic field probes (SQUIDs).

It is the aim of this invention to overcome the described disadvantages of the known state of the art. Specifically, it is the objective of this invention to provide, with an acceptable input in terms of synthesis technique, multiply modifiable and thus variably applicable, pharmacologically and toxicologically safe magnetic particles which can be prepared under thermally sterilized and aseptic conditions.

Surprisingly, the attempt to meet the catalogue of pharmaceutical demands for medical use has been successful owing to glycosaminoglycan coated magnetites.

The subject of this invention is therefore nanocrystalline magnetic particles consisting of a magnetic iron oxide core of $Fe_3O_4$, gamma-$Fe_2O_3$ or mixture thereof and an envelope chemisorbed to this core. These are characterized by composition of the coating material of natural or synthetic glycosaminoglycans and/or derivatives thereof with molecular weights of 500 Da to 250,000 Da, if necessary, covalently cross-linked by appropriate cross-linking agents and/or modified by specific additives.

The chondroitin magnetites, according to the invention, can be classified as physiologically safe. Chondroitin is considered a glycosaminoglycan and is of animal or human origin. It is of ubiquitous presence in the body and has numerous medical applications. The iron oxide core presents no difficulties—as long as it is properly shielded by coating material. After intracellular dissolution of the iron oxide core, the liberated iron is incorporated in the endogenous iron pool. Chondroitin magnetites exhibit extremely good tolerance following heat sterilization with LD50 values of 20 mmol/kg (rat and mouse). Well defined imaging of tumors/metastases has been obtained even from doses as low as 10 μmol/kg. This has provided an almost unprecedented safety margin of 2000. Furthermore, glycosaminoglycans are characterized by high hydrolytic stability of the glycosidic bond.

The entire range of demands can be met by these glycosaminoglycan coated magnetic iron oxide particles: homogeneous iron oxide core, chemical stability of the coating material with well known positive activity spectrum, preparation of nanocrystalline magnetic particles under non-invasive conditions, expansion of synthesis according to the modular principle (starting from a basic body, specific task oriented modifications can be added), high efficiency of diagnostic and therapeutic action, good tolerance, no significant side effects, no necessary additives to avoid possible side effects, higher margin of safety (factor 2000 as MR tumor/metastases diagnostic agent), continued galenic stability even after adjustment of the isotonic value with salt and after heat sterilization in the final receptacle and low number of decomposition products after extended storage. On the other hand, dextran magnetite, protein magnetite, gum arabic gelatin magnetite or magnetite with synthetic coating materials can only partially satisfy the catalogue of demands. According to the invention, if the particles are used in therapy, the magnetic core can be doped with 6Li, 57Fe, 61Ni, Ni, 67Zn, Zn, Mn, 99Ru, 101Ru, 113Cd, 119Sn, 121Sb, 127I, 151Eu, 155Gd, 156Gd, or 157Gd.

Especially preferred design variants of the magnetic particles are, according to the invention, characterized by the following features:
 the core consists of magnetic iron oxide with core diameters being smaller than the dimension of the individual magnetic domains and/or
 they are available with the common pharmaceutical adjuvants for injectable solutions and/or enteral agents as stable aqueous colloid dispersion solutions which are 0.2 μm filterable and can be thermally sterilized and/or the core, if doped is preferably doped with $^6$Li, $^{57}$Fe, $^{61}$Ni, $^{151}$Eu, $^{157}$Gd and/or the natural or synthetic glycosaminoglycans are chondroitin sulfates, dermatan sulfates, heparan sulfates, heparin and their synthetic analogues or other heparinoids and/or the coating material, after the preparation of the coated magnetic iron oxide particles, is additionally cross-linked by cross-linking agents common in biochemistry and the chemistry of natural substances and/or mono- di-, tri-, and oligoamines and/or synthetic and biological oligopeptides and proteins are bonded to the coating material and/or reduced or oxidized glutathione is bonded to the coating material and is cross-linked with intraparticular reversibility and/or surface-active substances are bonded to the coating material and/or targetable structure substances, preferably hormones, cholesterol, lipids, ether lipids, proteins, monoclonal antibodies, lectins, tumor lectins, adhesion proteins, fusion proteins, transport proteins and transport units, alkaline proteins, such as histones, interleukins, lipoproteins, for example, LDL, glycolipids, interferons, tumor-necrosis factors, protein A and adjuvants residual glycosyl and general sugar residues which play a role in complement and immune recognition as well as ribonucleic and deoxyribonucleic acid and their fragments and structural elements or mixtures thereof, if necessary with the addition of chemotherapeutic agents, preferably cytostatic agents, are bonded to the coating material and/or cross-linking, bonding of targetable structures and/or surface-active substances can be combined as desired, they are surrounded by cage molecules, preferably consisting of subunits of clathrins and/or synthetic analogues.

The subject of the invention is also the method for the preparation of nanocrystalline magnetic particles consisting of a magnetic iron oxide core of Fe$_3$O$_4$, gamma-Fe$_2$O$_3$ or a mixture thereof and a chemisorbed envelope or coating on the core. The method, characterized by the synthesis of iron oxide cores and the coating thereof, taking place, if necessary, under biomimetic conditions (with the term biomimetic in this context defining a synthesis method under circumstances close to physiological conditions pH 6–8, T≦37° C., p =1 bar, aqueous solution), if necessary with free functional groups of the coating material activated and intraparticularly cross-linked with the coating by addition of cross-linking agents and the cross-linked coating modified by additives of surface-active substances, targetable structure substances—if necessary with addition of chemotherapeutic agents and/or low-molecular weight substances, as the case may be.

Especially preferred design variants of the present method, according to the invention, are characterized by the following features:

natural or synthetic glycosaminoglycans or derivatives thereof, preferably chondroitin sulfates, dermatan sulfates, heparan sulfates, heparin and synthetic analogues thereof are used as coating substances, and/or the functional groups of the coating material of the magnetite stock solution are activated with water soluble carbodiimide derivatives or in a two-phase system with lipophilic carbodiimides, thereafter the activated magnetite is purified and isolated and/or bifunctional cross-linking agents common in biochemistry and in the chemistry of natural products and/or mono-, di-, tri-, and oligoamines, synthetic or biological oligopeptides, reduced or oxidized glutathione are added to the activated magnetite solution, with non-reacted educts being non-invasively separated by dialysis and the magnetite cross-linked and/or with its hydrophilia altered to be adjusted to its desired final concentration and/or surface-active substances are admixed and added to the activated magnetite solution and/or the activated magnetite solution getting added to it targetable structure substances, preferably hormones, cholesterol, lipids, tumor lectins, adhesion proteins, fusion proteins, transport proteins, and transport units, alkaline proteins such as histones, interleukins, lipoproteins, for example, LDL, glycolipids, interferons, tumor-necrosis factors, protein A and adjuvants, compounds which contain residual sugar, which plays a role in complement and immune recognition, as well as ribonucleic and deoxyribonucleic acids as well as fragments and structural elements thereof or a mixture thereof and/or chemotherapeutic agents are admixed to the activated magnetite solution or are added to the magnetite and/or lower molecular weight substances affecting the physiological distribution pattern of the particles are admixed and added to the activated magnetite solution and/or clathrin is admixed to the activated magnetite solution.

Furthermore, the invention relates to diagnostic and/or therapeutic agents characterized by iron oxide cores of FE$_3$O$_4$, gamma-Fe$_2$O$_3$ or mixtures thereof which are isotope doped with $^6$Li, $^{57}$Fe, $^{61}$Ni, Ni, $^{67}$Zn, Zn, Mn, $^{99}$Ru, $^{101}$Ru, $^{113}$Cd, $^{119}$Sn, $^{121}$Sb, $^{127}$I, $^{151}$Eu, $^{155}$Gd, $^{156}$Gd, or $^{157}$Gd, as the case may be, and are surrounded by a biodegradable coating of natural or synthetic glycosaminoglycans and/or derivatives thereof with molecular weights from 500–250,000 Da, with the coating molecules being cross-linked with a cross-linking agent and modified by surface-active substances, targetable structure substances and residues of lower molecular weight, depending on need.

Especially preferred design variants of the agents, according to the invention, are characterized by the following features:

the core, if doped, is preferably doped with $^6$Li, $^{57}$Fe, $^{61}$Ni, $^{151}$Eu, $^{157}$Gd and/or the natural or synthetic glycosaminoglycans are chondroitin sulfates, dermatan sulfates, heparan sulfates, heparin and their synthetic analogues which are cross-linked with bifunctional cross-linking agents common in biochemistry and the chemistry of natural products and/or are crosslinked with mono-, di-, tri-, and oligoamines, synthetic and biological oligopeptides, reduced or oxidized glutathione and/or surface-active substances are bonded to the cross-linked coating and/or the cross-linked coating getting bonded to it targetable structure substances, preferably hormones, cholesterol, lipids, ether lipids, proteins, monoclonal antibodies, lectins, tumor lectins, adhesion proteins, fusion proteins, transport proteins, transport units, alkaline proteins, such as histones, interleukins, lipoproteins, for example, LDL, glycolipids, interferons, tumor-necrosis factors, protein A and adjuvants, compounds which contain residual sugar which plays a role in complement and immune recognition as well as ribonucleic and deoxyribonucleic acids as well as fragments and structural elements thereof or mixtures thereof, if necessary, with addition of chemotherapeutic agents, preferably cytostatics and/or subunits of clathrin surround the enveloped particles in cage form and/or the magnetic particles are incorporated in liposomes, chylomicrons, cells, cell organelles bacteria, virus shells and are surrounded by lipids in the form of a double layer.

The invention is also related to the use of diagnostics and/or therapeutics in the preparation of diagnostic and/or therapeutic agents for radiotherapy, hyperthermia, chemotherapy and MR diagnosis as well as biomagnetic probes.

In contrast to the particles of the present state of the art, the nanocrystalline particles described herein are constructed according to the modular principle. Based on a parent substance which consists of a magnetic iron oxide core and an envelope of, for example, glycosaminoglycan, they can be modified in solution according to the purpose of application.

Such modifications can be achieved by covalent or non-covalent adding, activation and/or cross-linking as well as by combination thereof. It has proven helpful to first cross-link the coating material in vitro before coupling the targetable structures. Coupling of targetable structures without prior cross-linkage might cause destabilization of the magnetic particles. The parent substance can thus be supplemented with targetable structures and addition of chemotherapeutic agents for application to selective tumor diagnostics/therapy. In addition, there are plenty of possibilities to modify the parent substance itself. This diversity is associated with a wide spectrum of applications. One can differentiate between the parent substance which is identified and taken up by the reticuloendothelial system (RES) due to its particular nature and serves, for example, MRI contrasting of liver and spleen tumors (metastases). Targeting of other organs/tissues can be achieved after parenteral administration by extending retention in the blood stream, acceleration of the extravasation and organ or tissue selection by attachment of targetable structures. Uptake by the RES is perceived as a reaction parallel to the reaction with the target organ and can be influenced by size, charge, surface, hydrophobia and pre-saturation of the RES.

The chemisorbed coating substances used are biodegradable substances of animal/human origin which are capable of stabilizing the iron oxohydroxy complex and of ensuring a synthesis of the coated iron oxide under biomimetic conditions.

Precipitation of the iron oxide at alkaline level can thus be avoided. The stock sols can be prepared from blood isotones, for example, by addition of mannitol and stable NaCl. The size of the emerging particles can be controlled during synthesis, for example by proper choice of the chondroitin/iron ratio and must not be adjusted to a fixed value by fractionation procedures.

No organic solvents are used in the preparation process. In contrast to dextran magnetites, particle stability is guaranteed in several organic solvents. The substances are useful in many diagnostic and therapeutic areas. Chemical bonding of coating molecules to the iron oxide core as described in the European patent application (publication number 0284549) is avoided in order to guarantee the biological degradability. The animal/human origin of the coating material is reflected in good tolerance. "Pro drug" forms and coating substances with pH dependent fracture sites can also be produced.

The envelope of glycosaminoglycan with carboxylic acid groups ensures solid chemisorbtion to the iron oxide core (and with the sulfuric acid and the residual N-acetyl also provides for the sufficient stability of the sol). The iron oxide core in this context is sufficiently shielded so that, in contrast to the majority of the conventional formulations, physiological incompatibilities with parenteral application are adequately compensated.

Possible coating materials are water soluble glycosaminoglycans like chondroitin sulfates, keratan sulfates, dermatan sulfates, heparin, hyaluronic acid, heparan sulfates and synthetic analogues. (Hyaluronic acid is often considered as one of the four primary representatives of glycosaminoglycans [mucopolysaccharide polysulfuric acid esters] as mentioned before). Hyaluronic acid differs from chondroitin sulfate, keratan sulfate, dermatan sulfate heparan (heparin) sulfate in that it does not contain any residual sulfuric acid and is itself not protein conjugated, but it promotes the proteoglycan aggregation. Glycosaminoglycans together with connecting tissue proteins form the ubiquitously present proteoglycans.

In the context of conventional wet chemical procedures of magnetite preparation, acidic Fe(II) : Fe(III) solutions are adjusted at increased temperature to a pH value at alkaline level by adding lye (e.g. NaOH, $NH_4OH$). The forming magnetite precipitates in the presence of the coating agent and entrains it, or the coating agent is added after formation of the magnetites. In some cases, ultrasound is applied during magnetite synthesis and leads to reduction in size of the forming particles (Menz et al. WO 900/295). The subsequent steps include peptization, neutralization, purification, addition of stabilizers as well as filling and heat sterilization—if possible—in the final receptacle.

These procedures which differ slightly from each other by initial concentrations, reaction temperatures, rates of adding, choice of the coating agent and the processing steps, the methods described here result in formation of glycosaminoglycan coated magnetites in a neutral medium (pH 7) and in ambient temperatures. Also, ultra sonic treatment is unnecessary. The pH value can be held constantly neutral in a chemostat. The alkaline range in which many coating agents and biological materials are hydrolytically instable can be completely avoided. This proves to be a significant advantage, since the number of possible decomposition products can thus be kept low.

According to the invention the glycosaminoglycans of the magnetites provide for almost complete shielding of the surface, so that specific interactions are minimized or avoided. Extensive hydrate coating is under discussion for erythrocytes as a result of the poly-N- acetyl-lactosamines (J. Vitala and J. Järnefelt, TIBS, October 1985, 392–395). It appears to be important for macrophage uptake of the parent substance that the coating surrounding the core does not cause any specific reactions, yet still be activated by the immune system so that the opsonized particles are taken up by the macrophages. Choice and derivation of the coating (charge and hydrophobia) in addition to size, offer a possibility, for other purposes, to passively influence extracellular interaction of the magnetites. Moreover, direct drug targeting is possible by attachment of specific recognition tags (e.g. monoclonal antibodies, hormones, guide proteins). Similar to the wide range of liposome applications, the interactions of parenterally applied particles so far have only been phenomenologically understood and are a current field of biochemical, pharmacological and medical research.

According to the invention, the described magnetic iron oxide particles which (with or without additional doping) together with a coating of glycosaminoglycan and the derivatives thereof or the synthetic analogous substances provide the advantage that the coating materials are biodegradable products. Iron is liberated from the iron oxide following the intracellular uptake and is incorporated into the iron pool (hemoglobin, iron storage proteins). The normal iron pool of an adult is increased only insignificantly by one single application of 10–30 µmol/kg body weight, a dose normally sufficient for diagnostic MR tomography. Extreme pH values can be avoided with the underlying synthesis, except for dissolution of the salts of iron so that the susceptibility to hydrolysis and/or pH induced chemical modification of the coating material is of minor importance.

Iron oxide particles dissolved in water with a coating of glycosaminoglycan represent the stock solution. The physical and pharmacological parameters of the particles can be influenced in situ by attaching lower and higher molecular substances/ligands/guide structures and by cross-linking as well as inclusion in and addition to cells or cell components—as described in the following examples. This actually enables adaptation to specific diagnostic and/or therapeutic problems. The approach has been so chosen that the premade magnetites (made according to Example 1 or 2) are transformed by activation of reactive groups into a form which allows coupling in a physiologically acceptable form to the appropriate ligands/spacers/substrates/targetable structures.

EXAMPLE 1

(Conventional Synthesis)

18.24 gm chondroitin-4-sulfate (Sigma Type A) is dissolved under heat in 400 ml of distilled water and gassed with nitrogen. 20.6 gm of Fe(II) chloride are dissolved under nitrogen in 210 ml of 1 M Fe(III) chloride solution. The freshly prepared Fe (II)/Fe(III) solution is slowly added drop-wise ($\approx 0.5$ ml/min) under nitrogen rinse to the 75° C. chondroitin sulfate solution so that the precipitate formed at the point of dripping is immediately dissolved. Then, previously degassed 3N NaOH solution is slowly added. The solution is then titrated to pH 10. Immediately thereafter, it is neutralized and boiled for 3 h on the reflux side and is continuously regulated in the process to pH 7. After cooling to room temperature and centrifuging (10 min., 3000 RPM) the supernatant solution is diafiltered with 10 l distilled water over a 3 kDa hollow fiber cartridge and is then reduced in a rotary evaporator to a volume of 250 ml. The pH value is adjusted to 7. After 0.2 µm filtration the ready-to-use solution is autoclaved at 121° C. The yield amounts to 100% relative to the employed iron.

EXAMPLE 2

(Biomimetic Synthesis)

5.0 gm chondroitin-4-sulfate are dissolved in 200 ml iron III hydroxide sol, corresponding to 6.6 mM Fe (see Jander/Blasius, Lehrbuch der analytischen and präparativen anorganischen Chemie, S. Hirzel Verlag, Stuttgart). Possible cloudiness is filtered off. A nearly neutralized solution of 1,282 gm ammonium iron(II) sulfate hexahydrate is added dropwise to the solution heated to 37° C., with the pH slowly drifting towards acidic being readjusted with diluted lye to physiological pH values. The completed magnetite is purified and autoclaved, which provides for accelerated recuperation of possible fault positions of the magnetite crystals.

EXAMPLE 3

(Doping)

As in Example 1, except that 5% of the employed Fe(II) is replaced by $^{61}$Ni as a Mössbauer active isotope for use in the resonant nuclear absorption therapy. 19.57 gm FeCl$_2$ and 1.05 gm $^{61}$NiCl$_2$ are to be used instead of the 20.6 gm FeCl$_2$.

EXAMPLE 4

(Desulfatizing to Change the Hydrophilia)

10 ml chondroitin sulfate magnetite according to Example 2 are eluted over a Dowex cation exchanger and are neutralized with appx. 7.5 ml pyridine. Pyridinium salt of chondroitin sulfate magnetite is obtained following lyophilization. The salt is dissolved in DMSO/ethanol or DMSO/H$_2$O and is maintained at 80° C. for 5 h. After cooling the solution is diluted with water and adjusted with NaOH to pH 9–9.5. This adjusted dispersion of desulfated chondroitin magnetite is dialysed against water, ultrafiltered (10 kDa) and filtrated under sterile conditions.

EXAMPLE 5

(Activation of Free Carboxylic Acids)

1 ml chondroitin-4-sulfate magnetite according to Example 2 is diluted 1:10 in distilled water and the pH value is adjusted to 4.5 with HCl. Water soluble carbodiimide (1-ethyl-3(3-dimethylaminopropyl)-carbodiimide-HCl (EDC.Pierce)) is added under agitation in 1.5-fold surplus quantity (compared to the functional groups to be activated) and the pH value is held constant at 4.5 (1 h at 4° C.). On completion of reaction, the non-reacted educt is carefully separated by dialysis from the activated magnetite and the substance retained is lyophilized.

The EDC reaction will have to be modified, if consequent reactions are to be initiated with the EDC activated magnetite (e.g. coupling to biogenic ligands) which are not stable at pH 4–5 or would lose biological activity. N-hydroxysulfosuccinimide (Sulfo-NHS, Pierce) must be added to the chondroitin magnetite or the reaction mixture of chondroitin magnetite and ligand and/or cross-linker for the coupling/cross-linking under physiological conditions or in the course of a biomimetic synthesis in order to enhance the stability of the intermediate product at physiological pH values and thus to increase yield and ensure biological activity. A stable intermediate product is obtained by adding sulfo- NHS (see Staros et al., Analytical Biochemistry 156, 220–222, 1986) in contrast to EDC reaction without sulfo-NHS additive where an O-acyl-urea derivative is intermediately formed which requires acidic reaction conditions and is sensitive to hydrolysis. The additional reagent has no influence on the final product. An amide bond is also produced in response to addition of an aminic ligand, and the lower molecular weight reagent is removed from the colloidal solution by dialysis of the ultrafiltration, following mediated condensation between acid and amine components.

EXAMPLE 6

(Desulfatized EDC).

10 ml desulfatized chondroitin magnetite, prepared according to Example 4, are converted with EDC according to Example 5. This results in activated magnetites which, due to reaction with the acid group of the coating material, is negatively charged or neutral depending on EDC content.

EXAMPLE 7

(Condensation with Glucosamine)

Magnetite solutions, according to Example 5 are mixed with 1.5-fold surplus quantity of glucosamine. An amide bond results from the condensation reaction between EDC activated carboxylic acid and glucosamine. The resulting magnetite, which has undergone change in hydrophilia, is dialyzed against distilled water and adjusted to the desired concentration.

EXAMPLE 8

(Cross-linking with Ethylene Diamine)

As in Example 7, but bifunctional ethylene diamine is added instead of glucosamine. In order to avoid interparticular cross-linking, the latter is done at lower magnetite concentrations with these concentrations being increased on completion of cross-linkage.

EXAMPLE 9

(Transferring Coupling)

10 ml magnetite solution, according to Example 5, with pH adjusted to 7.4, are mixed with 10 ml (10–20 mg/ml) human transferrin which had been transformed into biologically active Fe(III) transferrin using appx. 10-fold molar surplus of iron(II) in a phosphate citrate buffer. The mixture is agitated for 6 h at 4° C., with the pH value being maintained at the physiological level. This is followed by ultrafiltration at 4° C. in order to separate the unbonded transferrin. The chondroitin magnetite which is not cross-linked or bonded with Fe transferrin and the chondroitin magnetite that is bonded with biologically non-active transferrin are separated by CNBr Sepharose 4 B (Pharmacia) previously bonded with anti-H-transferrin (see van Ejik and van Noort, J. Clin. Chem. Clin. Biochem., Vol. 14,475–478, 1976). This is followed by an assay of content and after adjustment of desired final concentration, by sterile filtration. Yield of iron: transferrin=1.1 to 5.1 (w/w). Storage is at 4° C., with the stability relative to native transferrin being significantly improved, as is known for immobilized proteins. Other targetable structures, such as monoclonal antibodies and/or cytostatic agents, can be coupled to the EDC activated magnetite (Example 5), according to the same reaction pattern.

EXAMPLE 10

(Hydrophobic Magnetite) 1 gm chondroitin magnetite lyophilized according to Example 1 is mixed with 100 ml DMSO/acetone and acidified. Dicyclohexylcarbodiimide (5-fold surplus quantity relative to carboxylic acid) is subsequently added to the solution mixed with the lipophilic amine benzylamine in 2-fold surplus quantity relative to carboxylic acids. The result is hydrophobic magnetite. The magnetites are 50 nm in size in ethanol (70 nm in water).

EXAMPLE 11

(Lipid Double Layer Magnetite)

As in example 7, however phosphatidylethanolamine (cephalin from egg yolk) is stoichiometrically (relative to EDC group) added as the amine component under $N_2$ and maintained at 4° C. for 2 h. The cephalin displaces the EDC with the ethanolamine head group and bonds to the chondroitin magnetite. A complete double layer is formed by addition of phosphatidylcholine (lecithin) in a 1.5-fold surplus quantity, relative to the cephalin or by a mixture of lecithin and cholesterol. Change of the solvent (EtOH water mixture) proves to be advantageous during the cephalin formation. The ethanol must be removed to enable formation of the double layer.

EXAMPLE 12

(Clathrin Cages)

Clathrin is isolated in monomeric form by well known procedures (see Review B. M. F. Pearse & R. A. Crother, "Structure and Assembly of Coated Vesicles", An. Rev. Biophys. Biophys. Chem. 16, 49–68 (1987)). Addition of premade magnetites (see Examples 1, 2) in Fe: protein=1:1 to 5:1 ratio (w/w) is followed by condensation of the clathrin monomers to typical clathrin cages by reduction of pH to 6.2 and addition of $MgCl_2$. Magnetites which were not incorporated in the process of condensation and empty clathrin cages are chromatographically separated from bonded cages.

EXAMPLE 13

(Small Magnetites)

Preparation of chondroitin magnetite according to Example 2 is so modified that the reaction solution is repumped through a filter cartridge with some of the magnetite particles appearing in the filtrate. In this manner especially small magnetites are produced which are highly suitable for intravenous lymphography and have a longer half-life in blood.

EXAMPLE 14

(Erythrocyte Inclusion)

Erythrocytes are separated from the other blood components in the customary fashion and mixed with physiological NaCl solution. The premade magnetites are added (0.56 mg/ml Fe to 1 mg/ml protein). The solution is subsequently pressurized with 50 bar nitrous oxide at 37° C. according to Disclosure DE 3812816 A1. Following pressure relief, non-included magnetite is separated by centrifugation. The result is erythrocyte envelopes which have taken up magnetite in a non-invasive process.

Figure 1:
FIG. 1.
Figure 5:
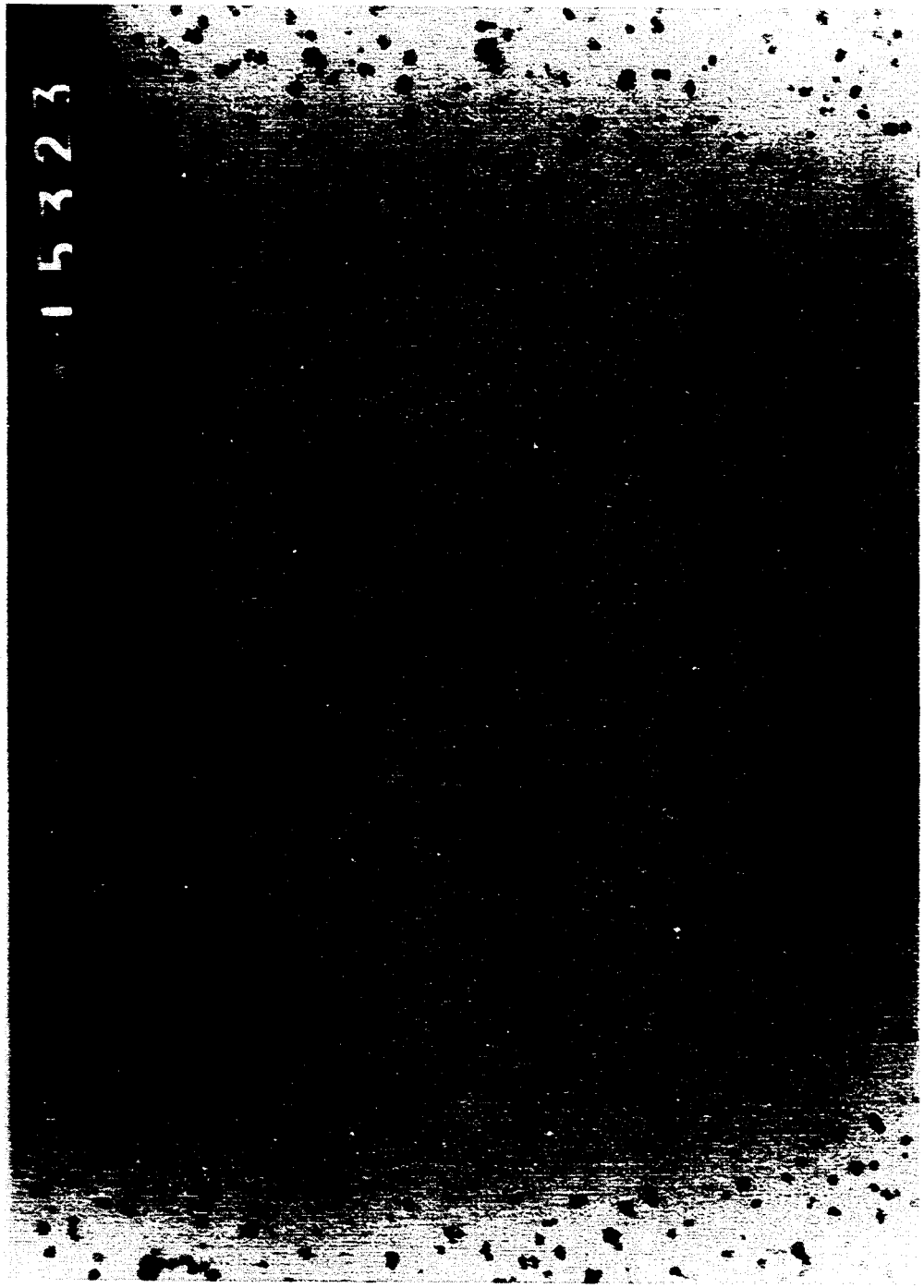

MR image. Axial slice of a mouse liver before (baseline) and 1, 10, and 30 minutes after application of 10 µmol/kg of chondroitin magnetite (chondroitin-4-sulfate) prepared according to Example 1. CSI GE 2T. Magnetites are taken up by the RES in clinically intact liver tissue takes up the magnetites so that the signal is extinguished. Tumor or tumor metastases have no RES and consequently cannot take up magnetite and do not exhibit any variation in signal intensity. The metastases are not visible in the baseline image, but are clearly distinguishable from the intact liver tissue in response to a dosage of as little as 10 µmol/kg.

FIG. 2:

Kinetics of magnetite degradation in rat liver for chondroitin magnetite prepared according to Example 1 (chondroitin-4-sulfate). Represented is the relative intensity (MRI liver signal/MRI reference signal) in percent of the baseline value following intravenous administration of 20 µmol/kg chondroitin magnetite as a function of time.

FIG. 3:

Dosage dependence. Represented is the relative intensity (MRI liver signal/MRI reference signal) 24 h after intravenous administration of chondroitin magnetite (prepared according to Example 1) as a function of the applied dosage.

FIG. 4:

X-ray diffractogram of a lyphophilized transferrin magnetite conjugate prepared by periodate activation of chondroitin-4-sulfate-magnetite and subsequent coupling to transferrin. The lines can be labelled cuboid in the manner of a spinel structure. The X-ray diffractogram shows the magnetite structure remains intact even after periodate activation.

FIG. 5:

Electron microscopic representation of the transferrin magnetite conjugate (see FIG. 4); magnification is 1:300,000. The electron edited magnetite core is clearly visible. No aggregates appear.

TABLE

| | |
|---|---|
| Table 1: | Data of chondroitin magnetite (chondroitin-4-sulfate) prepared according to Example 1. |
| Size: | 52 nm (with laser light diffraction) |
| Relaxivity: | $T_1$ 40 1/mmol0s |
| | $T_2$ 120 1/mmol0s |
| Fe concentration | 0.33M |
| Acute tolerance | |
| $LD_{50}$ (mouse) | 25 mmol/kg |
| Half-life in blood (with a dosage of 100 µmol/kg in rat) | 4.4 min. |

We claim:

1. Nanocrystalline magnetic particles consisting of a magnetic iron oxide core of $FE_3O_4$, gamma-$Fe_2O_3$ or mixtures thereof and a chemisorbed coating on this core, wherein composition of the coating material of natural or synthetic glycosaminoglycans and/or derivatives thereof with molecular weights of 500 Da to 250,000 Da combined, optionally covalently cross-linked by appropriate cross-linking agents and/or modified by specific additives.

2. Magnetic particles according to claim 1 wherein said particles have core diameters smaller than the dimensions of the magnetic singular domains.

3. Magnetic particles according to claim 1 wherein said particles optionally are available with the common pharmaceutical adjuvants for injectable solutions and/or enteral agents as stable aqueous colloid dispersive solutions which are 0.2 µm filterable and optionally can be heat sterilized.

4. Magnetic particles according to claim 1 wherein the natural or synthetic glycosaminoglycans are chondroitin sulfate, dermatan sulfate, heparan sulfate, heparin and synthetic analogues thereof or other heparinoids.

5. Magnetic particles according to claim 1 wherein the coating material after preparation of enveloped magnetic iron oxide particles, is additionally cross-linked by cross-linkers common in biochemistry and chemistry of natural products.

6. Diagnostic and/or therapeutic agents comprising optionally isotope doped iron oxide cores of $FE_3O_4$, gamma-$Fe_2O_3$ or their mixtures, which are surrounded by a biodegradable coating of natural or synthetic glycosaminoglycans and/or derivatives thereof with molecular weights between 500–250,000 Da, with the coating molecules possibly being cross-linked by cross-linking agents and modified by surface-active substances, targetable structure substances and lower molecular weight residues.

7. Diagnostic and/or therapeutic agents according to claim 6 wherein the natural or synthetic glycosaminoglycans are chondroitin sulfate, dermatan sulfate, heparan sulfate, heparin and their synthetic analogues which are cross-linked by bifunctional cross-linking agents common in biochemistry and chemistry of natural products and/or are cross-linked with mono-, di-, tri-, and oligoamines, synthetic and biological oligopeptides, reduced or oxidized glutathione.

8. Magnetic particles according to claim 1 wherein the glycosaminoglycan is chondroitin sulfate, keratin sulfate, dermatan sulfate, hyaluronic acid, heparan sulfate or synthetic analog thereof.

9. Magnetic particles according to claim 1 wherein the glycosaminoglycan is chondroitin sulfate, keratin sulfate, dermatan sulfate, hyaluronic acid, or synthetic analog thereof.

10. Magnetic particles according to claim 1 wherein the glycosaminoglycan is chondroitin sulfate, keratin sulfate, dermatan sulfate or hyaluronic acid.

11. Magnetic particles according to claim 1 wherein the glycosaminoglycan is chondroitin sulfate or dermatan sulfate.

* * * * *